United States Patent [19]

Dubroeucq et al.

[11] 4,451,461
[45] May 29, 1984

[54] 10-(1-AZA-[2,2,2]-BICYCLO-3-OCTYL]-10H-2-PHENOTHIAZINESULFONAMIDE AND DERIVATIVES THEREOF

[75] Inventors: Marie-Christine Dubroeucq, Enghien-les-Bains; Jean E. M. A. Rataud, Paris, both of France

[73] Assignee: Pharmindustrie, Gennevilliers, France

[21] Appl. No.: 395,235

[22] Filed: Jul. 6, 1982

[30] Foreign Application Priority Data

Jul. 10, 1981 [FR] France .................. 81 13602

[51] Int. Cl.³ .................. A61K 31/54; C07D 453/00
[52] U.S. Cl. .................. 424/246; 544/42; 544/43
[58] Field of Search ............ 544/42, 43; 424/246

[56] References Cited

U.S. PATENT DOCUMENTS 3,987,042 10/1976 Gueremy .................. 544/43

FOREIGN PATENT DOCUMENTS 2034605 12/1970 France .

2318638 7/1975 France .

Primary Examiner—Richard Raymond
Attorney, Agent, or Firm—Beveridge, DeGrandi & Kline

[57] ABSTRACT

10-[1-aza-(2,2,2)-bicyclo-3-octyl]-10H-2-phenothiazinesulfonamides of the formula:

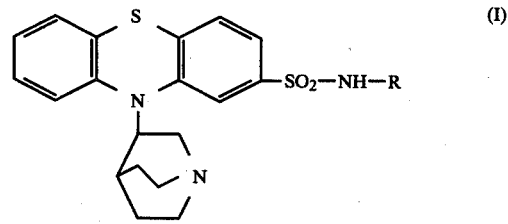

wherein R represents a hydrogen atom or an alkyl group having 1 to 3 carbon atoms are disclosed together with a process for their preparation. These compounds can be used as medicaments for the treatment of duodenal and gastric ulcers.

7 Claims, No Drawings

10-(1-AZA-[2,2,2)-BICYCLO-3-OCTYL]-10H-2-PHENOTHIAZINESULFONAMIDE AND DERIVATIVES THEREOF

The present invention relates to 10-[1-aza-(2,2,2)-bicyclo-3-octyl]-10H-2-phenothiazinesulfonamide and its N-monoalkyl derivatives which can be used as medicaments in particular for the treatment of gastric and duodenal ulcers.

The compounds of the present invention may be represented by the general formula:

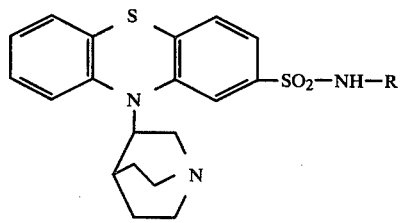

(I)

wherein R represents a hydrogen atom or an alkyl group having 1-3 carbon atoms. The compounds according to the invention may be prepared from N,N-dimethyl-10-[1-aza-(2,2,2)-bicyclo-3-octyl]-10H-2-phenothiazinesulfonamide, the preparation of which is described in French certificate of addition No. 75 23340 (No. 2,318,638).

The process according to the invention comprises four stages which may be represented as follows:

(a)
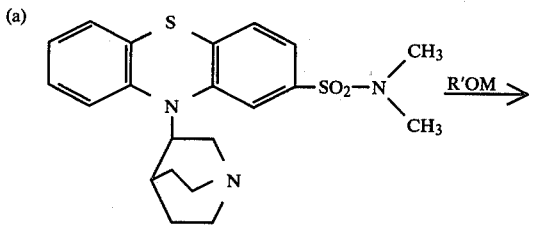

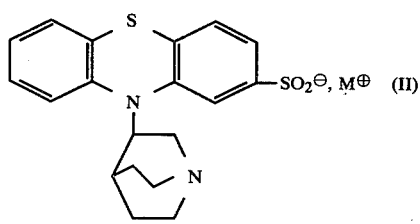
(II)

In formula (II) M represents an alkali metal atom such as sodium or potassium. R'OM represents an alkali metal alcoholate having 1 to 7 carbon atoms.

(b) (II) 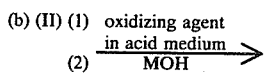

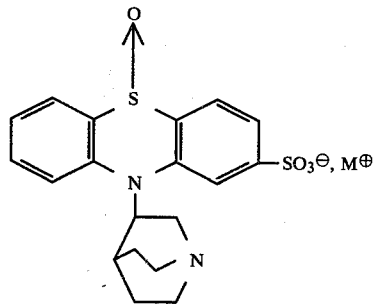
(III)

(c) (III) 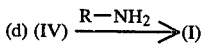
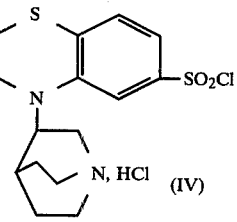
(IV)

(d) (IV) 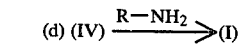 (I)

In order to effect reaction (a) N,N-dimethyl-10-[1-aza-(2,2,2)-bicyclo-3-octyl]-10H-2-phenothiazinesulfonamide is treated with an alcoholate in a solvent such as tetrahydrofuran under reflux or an alcohol having a high boiling point such as isoamyl alcohol under reflux or even a dipolar aprotic solvent such as dimethylsulfoxide at a temperature exceeding 80° C. A useful process consists in using potassium tertiobutylate in dimethylsulfoxide at 100° C.

Stage (b) consists in oxidizing the sulfinate group into a sulfonate group. In the course of this reaction oxidation of the sulfur atom of the phenothiazine ring into sulfoxide is also taking place. To effect such reactions, the compound of formula (II) is treated with an oxidizing agent in an aqueous medium together with at least 2 equivalents of a strong acid (e.g., methanesulfonic acid). To achieve this, known oxidants capable of transforming a sulfinic acid to a sulfonic acid are used (cf. Comprehensive Organic Chemistry, Vol. 3, p. 317, K. K. Andersen, Sulfinic acids and their Derivatives, Pergamon Press, 1979). A useful method comprises the use of sodium metaperiodate in water, in the presence of methanesulfonic acid at ambient temperature. At the end of the reaction, the mixture is rendered alkali using an alkaline metal hydroxide MOH; finally an alkali metal salt of 10-[1-aza-(2,2,2)-bicyclo-3-octyl]-10H-phenothiazine 5-oxide 2-sulfonic acid of formula (III) is obtained.

In stage (c) the compound of formula (III) is subjected to the action of thionyl chloride which on the one hand reduces the sulfoxide function thus regenerating the sulfur atom of the phenothiazine ring, and on the other hand transforms the sulfonate group into a sulfochloride group. An inert solvent at a temperature of between 60° and 150° C. is used, preferably in the presence of dimethylformamide as catalyst. A useful method comprises the use of toluene under reflux containing between 0.5 and 2% dimethylformamide. The hydrochloric acid released during the reaction salifies the compound formed which is ultimately obtained in hydrochloride form mixed with the alkali metal chloride formed. This mixture is used as such in the following stage.

In stage (d) the product obtained is treated with an excess of the appropriate amine of formula R—NH$_2$. In the case of ammonia (R=H) liquid ammonia is advantageously used at its boiling point. In the case of alkylamines (R=alkyl) it is advantageous to operate in an inert solvent such as an aromatic hydrocarbon, e.g. benzene or toluene at ambient temperature.

The reaction mixtures obtained according to the process described above are treated according to conventional methods (evaporation, extraction by using solvents, distillation, crystallization, chromatography, etc.) so as to isolate the new compounds of formula (1) in a pure state. In the process of the invention, the compounds of formulas (II), (III) and (IV) are also new products.

The compounds of formula (I) in the form of a free base may be transformed into addition salts using an inorganic or organic acid, by the action of such an acid in the appropriate solvent. Suitable acids include hydrochloric, hydrobromic, sulfuric, methanesulfonic, fumaric, maleic, and tartaric acids.

The following examples illustrate the invention without limiting it.

EXAMPLE 1

10-[1-AZA-(2,2,2)-BICYCLO-3-OCTYL]-10H-2-PHENOTHIAZINESULFONAMIDE (a) Potassium 10-[aza-(2,2,2)-bicyclo-3-octyl]-10H-2-phenothiazinesulfinate.

4.48 g of potassium tetriobutylate were added to a solution of 4.15 g of N-N-dimethyl-10-[1-aza-(2,2,2)-bicyclo-3-octyl]-10H-2-phenothiazinesulfonamide in 60 ml of dimethylsulfoxide which was heated to 60° C. The mixture was stirred and heated to 100° C. for one hour. After cooling to the ambient temperature a few drops of water were added in order to destroy the excess potassium tertiobutylate. The solution was fixed over a silica column (500 g); methanol was the eluent. The top fractions contained dimethylsulfoxide. The product required was then drawn off. The methanol was evaporated and the residue taken up in 50 ml of ethanol. The white crystals formed were drained and dried. 2 g of 10-[1-aza-(2,2,2)-bicyclo-3-octyl]-10H potassium phenothiazinesulfinate which melted above 250° C. were obtained. I. R. Spectrum (KBr pallet): 980 and 1.020 cm$^{-1}$ (—SO$_2^-$).

(b) Potassium 10-[1-aza-(2,2,2)-bicyclo-3-octyl]-10H-phenothiazine 5-oxide 2-sulfonate.

A mixture of 8 g of potassium 10-[1-aza-(2,2,2)-bicyclo-3-octyl]-10H-2-phenothiazinesulfinate, 33.3 ml of an aqueous 1.25 N solution of methanesulfonic acid, 8.67 g of sodium metaperiodate and 300 ml of water was stirred for 16 hours at the ambient temperature. At the end of the reaction, a red solution with a slightly insoluble substance which was eliminated by filtration, was obtained. The filtrate was rendered alkaline at a pH of 11 by adding potassium hydroxide and was then evaporated to dryness at reduced pressure. The residue was fixed over a silica column and eluted with methanol. Once the eluted fractions had evaporated, 7.2 g of potassium 10-[1-aza-(2,2,2)-bicyclo-3-octyl]-10H-phenothiazine 5-oxide 2-sulfonate were obtained, which melted above 250° C. I. R. Spectrum (KBr pallet): 1.020 and 1.200 cm$^{-1}$ (—SO$_3^-$).

(c) 10-[1-aza-(2,2,2)-bicyclo-3-octyl]-10H-2-phenothiazinesulfonamide.

7 ml of thionyl chloride were added drop by drop to a stirred suspension of 6.6 g of potassium 10-[1-aza-(2,2,2)-bicyclo-3-octyl]-10H-phenothiazine 5-oxide 2-sulfonate in 150 ml of toluene. Heating under reflux took place for 30 minutes, then cooling to 50° C. and a solution of 2 ml dimethylformamide in 30 ml toluene was introduced drop by drop. The yellow suspension obtained was heated under reflux for 30 minutes and the excess solvent and thionyl chloride were evaporated at reduced pressure. The residue was suspended in 100 ml of toluene which was then evaporated. 7 g of a yellow solid comprising a mixture of 10-[1-aza-(2,2,2)-bicyclo-3-octyl]-10H-2-phenothiazine sulfonyl chloride in the form of its hydrochloride and potassium chloride were obtained.

(d) 1 g of this mixture was poured into 100 ml of liquid ammonia at −30° C. The ammonia was left to evaporate slowly. The residue was taken up in 50 ml of chloroform and 50 ml of water. The organic phase was decanted, dried over magnesium sulfate and evaporated. The residue was fixed over a silica column and eluted with methanol. 0.35 g were obtained which were suspended in 5 ml of isopropyl oxide. The crystals were drained and dried; 0.31 g of 10-[1-aza-(2,2,2)-bicyclo-3-octyl]-10H-2-phenothiazinesulfonamide which melted above 260° C. were obtained.

EXAMPLE 2

N-METHYL-10-[1-AZA-(2,2,2)-BICYCLO-3-OCTYL]-10H-2-PHENOTHIAZINESULFONAMIDE 7 ml of thionyl chloride were added drop by drop to a stirred suspension of 6.6 g of potassium 10-[1-aza-(2,2,2)-bicyclo-3-octyl]-10H-phenothiazine 5-oxide 2-sulfonate (prepared according to Example 1) in 150 ml of toluene. Heating under reflux took place for 30 minutes followed by cooling to 50° C. A solution of 2 ml of dimethylformamide in 30 ml of toluene was then introduced drop by drop. The yellow suspension obtained was heated under reflux for 30 minutes and the solvent and excess thionyl chloride were evaporated off under reduced pressure. The residue was suspended in 100 ml of toluene and the toluene was then evaporated off. 7 g of a yellow solid were obtained comprising a mixture of 10-[1-aza-(2,2,2)-bicyclo-3-octyl]-10H-2-phenothiazinesulfonyl chloride in the form of the hydrochloride and potassium chloride.

5.5 g of this mixture were added to 100 ml of toluene. 100 ml of a 10% by weight solution of methylamine in toluene were added drop by drop, while stirring, to the suspension obtained. The reaction mixture was stirred for 16 hours at ambient temperature and the solvent was then evaporated off at reduced pressure. The residue was fixed over a silica column and eluted with a mixture containing 9 parts by volume of chloroform and 1 part by volume of diethylamine. 3.5 g of the product was obtained which was recrystallized in 50 ml of acetonitrile. Finally, 2.3 g of N-methyl 10-[1-aza-(2,2,2)-bicyclo-3-octyl]-10H-2-phenothiazinesulfonamide which melted at 255° C. were obtained.

PHARMACOLOGICAL PROPERTIES

The anti-secretory activity of the compounds of formula (I) according to the invention has been investigated in cases of gastric hypersecretion which has been stimulated by pentagastrine in dogs fitted with the Heidenhein pouch.

Three mongrels, fitted with the Heidenhein pouch and not having eaten for 18 hours, were given a veinous perfusion of 4 mg/kg/hour pentagastrine, at a volume of 30 ml/hour for 4 hours. The secretion in the pouch was collected in a bottle which was changed every 15 minutes. 1.5 hours after commencement of the perfusion, the product to be investigated was administered orally in an h°000 gelatine-coated capsule. The effective dose 50% ($ED_{50}$) is the dose which reduces the hourly acid output by 50% during the 3rd or 4th hour of the experiment in relation to the acid output of the second hour of perfusion. The doses are expressed as a product in basic form.

As an example, the table below shows the results obtained with the product of Example 2.

| Products | $ED_{50}$ in mg/kg p.o. |
| --- | --- |
| Cimetidine | 2.3 |
| N,N—Dimethyl-10-[1-aza-(2,2,2)-bicyclo-3-octyl]-10H—2-phenothiazine-sulfonamide | 1.25 |
| Example 2 | 0.7 |

The products of the invention are powerful inhibitors of gastric secretion. The product of Example 2 in particular is more active than cimetidine.

TOXICOLOGICAL PROPERTIES

The acute toxicity of the compounds according to the invention have been established in male $CD_1$ (Charles River) mice following oral administration. The $LD_{50}$ has been calculated following 3 days of observation by the cumulative method of J. J. Reed and H. Muench (Amer. J. Hyg. 1938, 27, 493).

The compounds act as relatively non-toxic substances in mice because the $LD_{50}$ of the compounds is between 300 and 1,000 mg/kg.

THERAPEUTIC USE

The compounds of the invention and their pharmaceutically acceptable salts may be used in the treatment of mammals, e.g. humans, in the form of tablets, capsules, gelatine-coated pills, suppositories or in the form of ingestible or injectible solution, etc., as inhibitors of gastric secretion in the treatment of duodenal or gastric ulcers. The compounds may be administered in a therapeutically effective amount.

The posology depends on the effects desired and the method of administration used. For example, when administered orally, it will be between 50 and 500 mg of active substance per day, with unit doses of from 10 to 100 mg.

Appropriate pharmaceutically acceptable carriers, diluents and adjuvants may be used together with the compounds described herein in order to prepare the desired compositions for use in treatment of mammals according to the invention. The pharmaceutical compositions of this invention will contain the active compound together with a solid or liquid pharmaceutically acceptable nontoxic carrier. Suitable pharmaceutical carriers are described in "Remington's Pharmaceutical Sciences" by E. W. Martin. Such compositions will contain an effective therapeutic amount of the active compound together with a suitable amount of carrier so as to provide the form for proper administration to the host.

What is claimed is:

1. 10-[1-aza-(2,2,2)-bicyclo-3-octyl]-10H-2-phenothiazinesulfonamides of the formula

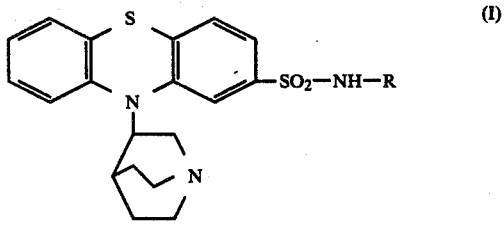

wherein R represents methyl.

2. A process for the preparation of 10-[1-aza-(2,2,2)-bicyclo-3-octyl]-10H-2-phenothiazinesulfonamides of the formula

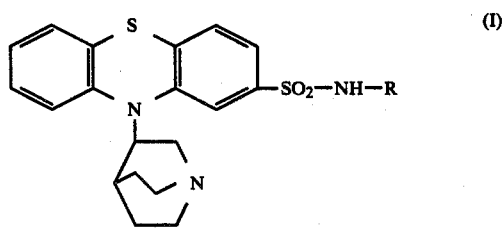

wherein R represents hydrogen or alkyl having 1 to 3 carbon atoms, which comprises reacting N,N-dimethyl-10-[1-aza-(2,2,2)-bicyclo-3-octyl]-10H-2-phenothiazinesulfonamide with an alkali metal alcoholate in a solvent, treating the sulfinate thus obtained with an oxidizing agent in an acid medium, rendering the solution alkaline by addition of an alkali metal hydroxide, subjecting the salt of 10-[1-aza-(2,2,2)-bicyclo-3-octyl]-10H-phenothiazine 5-oxide 2-sulfonic acid obtained to the action of thionyl chloride and reacting the reaction mixture obtained comprising sulfonyl chloride with a compound of the formula $R—NH_2$.

3. 10-[1-aza-(2,2,2)-bicyclo-3-octyl]-10H-2-phenothiazinesulfonic acid and its alkaline salt.

4. 10-[1-aza-(2,2,2)-bicyclo-3-octyl]-10H-2-phenothiazine 5-oxide 2-sulfonic acid and its alkaline salt.

5. 10-[1-aza-(2,2,2)-bicyclo-3-octyl]-10H-2-phenothiazine sulfonyl chloride.

6. An agent for inhibiting gastric secretion for use as a medicament in the treatment of duodenal and gastric ulcers comprising a compound according to claim 1 or its salt with a pharmaceutically acceptable acid, and a pharmaceutically acceptable carrier.

7. A method of treating a mammal afflicted with duodenal or gastric ulcers and to inhibit gastric secretion which comprises administering to said mammal a pharmaceutically effective amount of a composition containing a compound according to claim 1 or a pharmaceutically acceptable salt thereof in a pharmaceutically acceptable carrier therefor.

* * * * *